United States Patent
Tsai et al.

(10) Patent No.: US 10,860,528 B2
(45) Date of Patent: Dec. 8, 2020

(54) DATA TRANSFORMATION AND PIPELINING

(71) Applicant: Clover Health, Jersey City, NJ (US)

(72) Inventors: Jasmine Tsai, Jersey City, NJ (US);
Chris Hartfield, Jersey City, NJ (US);
George Leslie Waksman, Jersey City, NJ (US)

(73) Assignee: Clover Health, Jersey City, NJ (US)

( * ) Notice: Subject to any disclaimer, the term of this patent is extended or adjusted under 35 U.S.C. 154(b) by 170 days.

(21) Appl. No.: 16/222,790

(22) Filed: Dec. 17, 2018

(65) Prior Publication Data

US 2020/0192862 A1 Jun. 18, 2020

(51) Int. Cl.
*G06F 16/11* (2019.01)
*G06F 16/16* (2019.01)

(52) U.S. Cl.
CPC .......... *G06F 16/116* (2019.01); *G06F 16/162* (2019.01)

(58) Field of Classification Search
CPC .............................. G06F 16/116; G06F 16/162
USPC ........................................................ 707/692
See application file for complete search history.

(56) References Cited

U.S. PATENT DOCUMENTS

| | | | | |
|---|---|---|---|---|
| 7,111,075 B2* | 9/2006 | Pankovcin | ............ | G06F 16/258 709/246 |
| 10,311,076 B1* | 6/2019 | Bruhn | ................... | G16H 10/00 |
| 10,642,854 B2* | 5/2020 | Pattnaik | ................... | G06F 9/38 |
| 2015/0186821 A1* | 7/2015 | Wang | ..................... | G06Q 10/10 705/2 |
| 2015/0187036 A1* | 7/2015 | Wang | ..................... | G06Q 50/22 705/2 |
| 2016/0019299 A1* | 1/2016 | Boloor | .................... | G06F 16/36 705/3 |
| 2016/0292241 A1* | 10/2016 | Patterson | ............... | G16H 10/60 |
| 2018/0210935 A1* | 7/2018 | Yazicioglu | ............ | G06F 40/186 |

FOREIGN PATENT DOCUMENTS

WO  WO 2018/175435 A2 * 9/2018 ............. G06F 19/24

OTHER PUBLICATIONS

Meystre, S. M., et al., "Extracting Information from Textual Documents in the Electronic Health Record: A Review of Recent Research", IMIA Yearbook of Medical Informatics 2008, © 2008, pp. 128-144.*
International Search Report for PCT/US2019/066640, dated Mar. 17, 2020, 3 pages.*
Written Opinion of the International Searching Authority for PCT/US2019/066640, dated Mar. 17, 2020, 8 pages.*

* cited by examiner

*Primary Examiner* — Robert Stevens
(74) *Attorney, Agent, or Firm* — Lee & Hayes, P.C.

(57) ABSTRACT

Systems and methods for transforming and pipelining data are disclosed. For example, it may be desirable to parse out usable data and to transform the usable data found in files that may be received from different sources and that may be in different file types. Described herein are system and methods that provide functionality to allow for determining a file type of a file, parsing out usable data from the file, performing a series of transformations on the usable data, and generating a pipeline that includes the series of transformations. The pipeline may be monitored for error detection.

20 Claims, 7 Drawing Sheets

```
1  -Jane.dough@insurance.com
2
3    Inputs:
4      billing_entity_id
5      provider_id
6
7    Validation_queries:
8      -info: check that all billing entitles are here
9       query:
10         SELECT count(*)=0|
11         FROM (SELECT id as billing_entity_id) missing_billing_entities
12      -info: check that all providers are here
13       query:
14         SELECT count(*)=0|
15         FROM (SELECT id as provider_id) missing_providers
16    Output:
17      name: dwh_prod.fact_provider_billing_entities
18      doc: |
19        A fact table that represents the connections between a provider and the
20        billing entity.
```

DATA TRANSFORMATION AND PIPELINING

BACKGROUND

The use of data for analytics has become ubiquitous. A company may receive data for analytics in a variety of different formats or file types. The variety of ways in which this data may be received may cause meaningful analysis of the data to be too complicated and too expensive. Described herein are improvements in technology and solutions to technical problems that can be used to, among other things, generate data sets of sufficient quantity and quality to increase the accuracy of data analytics.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

DETAILED DESCRIPTION

Systems and methods for transforming and pipelining data are described herein. Take, for example, a data service including a system that has stored thereon and/or has access to one or more databases containing data, such as health-related data, for example. Such data may be used by the system for one or more purposes, such as predicting outcomes and/or events, determining fraudulent insurance claims, identifying at-risk patients, and the like. However, each source that provides the health-related data may provide the data in a different format or file type. For example, a pharmacy may send a list of filled prescriptions to the data service in a comma separated value (CSV) file while an insurance company may send a list of claims in an XML spreadsheet. Additionally, the file that includes the health-related information may include other types of information that the data service may not be interested in, such as non-health-related data. The data service may receive hundreds, or even thousands, of these files every day. Traditionally, a user would have to manually download each file and identify the relevant and/or the desired data because the immense volume of file types would not allow for the system to be automated. Increasing the ability to modify data in order to perform analyses may improve prediction accuracy and/or allow for more robust analysis techniques to be utilized.

The presently-disclosed systems and methods may be utilized to classify incoming files by file type, identify relevant information in a file, and provide functionality to allow a user (e.g., data analyst) to modify the relevant information in order to perform a desired analysis. For example, the system may receive files from multiple sources. Each source may provide their respective file in a different format or as a different file type. As each file is received, the system may identify a file type based at least in part on the content located within the file or metadata associated with the file and may determine a parser used to parse the file based at least in part on the file type. By way of example, each parser may be associated with a regular expression (regex) and the system may perform a regex search on each file that is received. When a sequence of characters or a pattern is identified within the file that matches the regex associated with a particular parser, then that parser is determined to be used for parsing the file. The parsers may have been previously generated by the system and associated with specific file types and/or regex such that when a file is received by the system, the system automatically identifies a parser to be used for parsing the information in the file. In some cases, a received file may be in a file type in which the system does not have a corresponding parser. In this case, the system may identify a similar file type to the file type of the received file and the system may select a parser associated with the similar file type to parse the received file. By way of example, parsing information from a file may include identifying usable data within the file at a certain location based at least in part on the type of file and the corresponding type of parser. Once the usable data within a file has been identified, the system may receive instructions to transform different sections of the data into a different format and to record each instance of a transformation in one or more tables associated with the respective sections of data. By way of example, a transformation of data may include an input and an output. Each input and output may include a file and/or a table that stores metadata, such as a transformation history, of the transformed data. As different sections of the file are transformed, the system may create a pipeline structure that stores a record of each transformation.

By identifying the usable data within a file and transforming the usable data as described above and elsewhere herein, the system provides functionality to allow users (e.g., data scientist, engineers, analysts, etc.) to manipulate different types of data from different sources and create an accessible pipeline that enables the user to follow a lineage of the transformed data.

For example, a system may receive multiple files of different file types from multiple different sources, such as a CSV file from a pharmacy that includes prescription-filling information and an XML, spreadsheet from a hospital that includes information on prescriptions as written. A user may wish to determine how many of the written prescriptions from the hospital were actually filled at the pharmacy. The system may determine an appropriate parser for each file based at least in part on the file type and may extract the usable data from each file. The system may then combine the appropriate usable data from each file as an input thereby transforming the data to create an output indicating the desired analysis. The output may be in the form of a table that correlates the data from both of the inputs. Each output can be further used as an input for further analysis, thereby generating a pipeline of transformations. Each input and output may include a file or a table that stores information associated with the transformed data.

By generating the pipeline of transformations, the system can also perform error monitoring for incoming files. For example, a series of transformations for particular types of data may be establish in order to obtain a desired analysis. The series of transformations may create an interconnected pipeline (e.g., a dependency graph or a directed acyclic graph (DAG)) where an output of one transformation depends on various outputs of previous transformations feeding into it. The system may receive a new file that includes an error, such as a zero value for a type of data used in one of the transformations that form the pipeline. The zero value may cause a cascading effect of errors throughout the interconnected pipeline. In this case, the system may monitor certain values of the pipeline and generate a notification to send to a device associated with a user indicating that a value is above or below a predefined threshold and that the target value (i.e., the desired value for the analysis) may be compromised. Additionally, the notification may include an indication of where in the pipeline the error has occurred, an input associated with the error, an output associated with the error, a parser associated with the error, a transformation associated with the error and/or which file the error originated from. In some cases, the notification may be sent to the device of the user and may cause an application on the device to initiate and to display the notification.

The present disclosure provides an overall understanding of the principles of the structure, function, manufacture, and use of the systems and methods disclosed herein. One or more examples of the present disclosure are illustrated in the accompanying drawings. Those of ordinary skill in the art will understand that the systems and methods specifically described herein and illustrated in the accompanying drawings are non-limiting embodiments. The features illustrated or described in connection with one embodiment may be combined with the features of other embodiments, including as between systems and methods. Such modifications and variations are intended to be included within the scope of the appended claims.

Additional details are described below with reference to several example embodiments.

Figure 1:
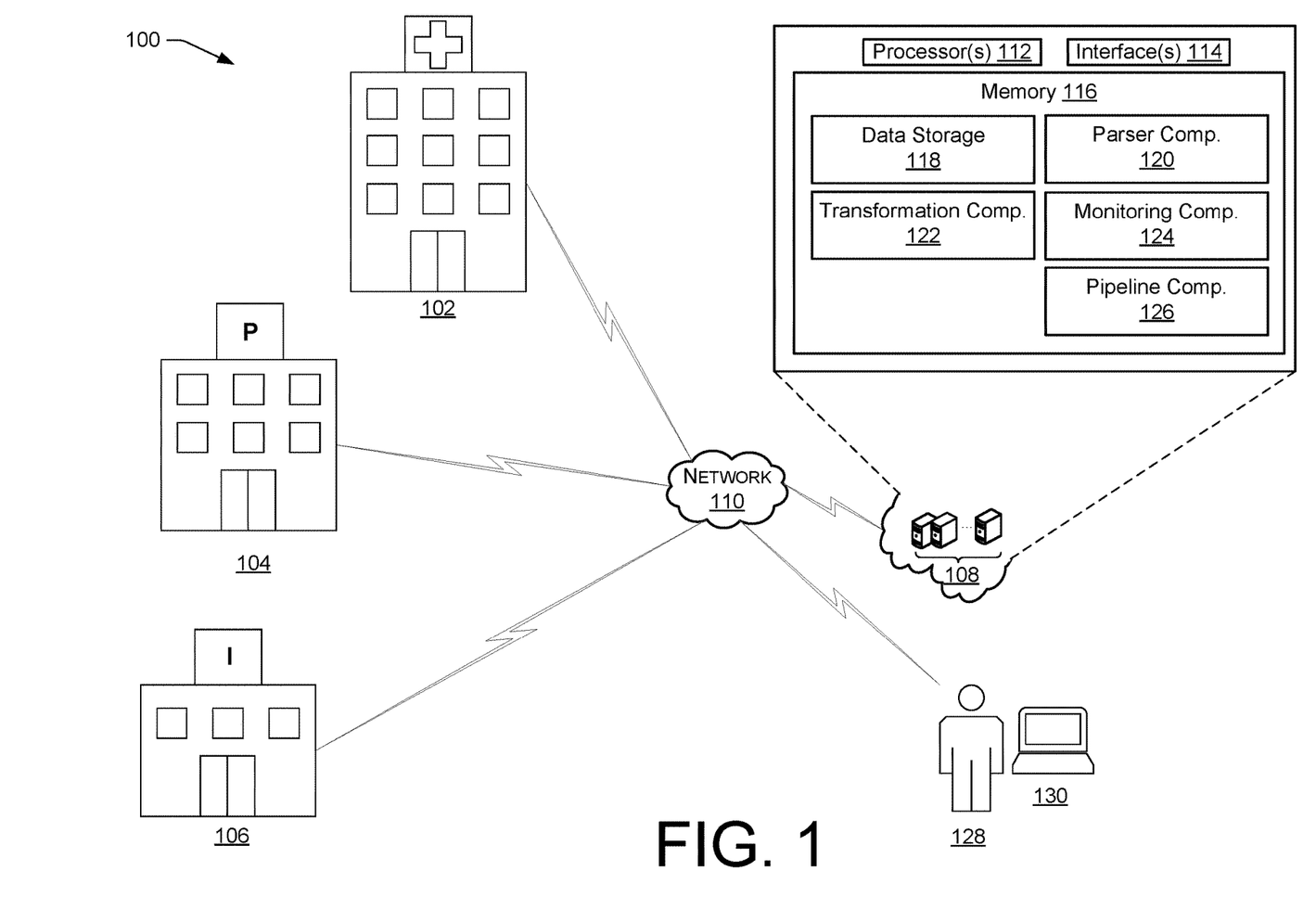
FIG. 1 illustrates a schematic diagram of an example environment for transforming and pipelining data.

FIG. 1 illustrates a schematic diagram of an example environment 100 for parsing, transforming, and pipelining data. The environment 100 may include a first data source 102, a second data source 104, and a third data source 106, for example. As shown in FIG. 1, each of the first data source 102, the second data source 104, and the third data source 106 represent a remote system that generates and/or acquires data associated with one or more people and stores that data, such as in a database associated with the first data source 102, the second data source 104, or the third data source 106. By way of example, the first data source 102 may be a hospital, clinic, and/or other type of healthcare provider. The second data source 104 may be a pharmacy that receives and fulfills prescriptions. The third data source 106 may be an insurance company that processes claims from the first data source 102, the second data source 104, or any other healthcare related entity.

It should be understood that while three data sources 102, 104, 106 are depicted in FIG. 1, the number of data sources may be one, two, three, or more than three. In examples, the number of data sources may be much more than three, such as thousands of data sources. It should also be understood that while the types of data sources have been depicted with respect to FIG. 1 as remote systems such as a hospital, a pharmacy, and an insurance company, the types of data sources may be any device that may receive input and generate data associated with a person based at least in part on that input. Further, while the examples provided herein are described with respect to data associated with a person or people, the data need not be specific to a person. For example, the data may be data associated with a device, a system, an entity that is not a person, an object, etc.

The first data source 102, the second data source 104, and/or the third data source 106 may communicate with a system 108 via one or more networks 110. The communication may include the sending and/or receiving of data associated with a person and/or people associated with a given data source. The system 108 may include one or more components, such as, for example, one or more processors 112, one or more network interfaces 114, and memory 116. The memory 116 may include one or more components, such as, for example, a data source 118, a parser component 120, a transformation component 122, a monitoring component 124, and/or a pipeline component 126. Each of the components of the memory 116 will be described below in detail.

The data storage 118 may be configured to store data received by the system 108. The data may by in any type of text document, binary document (e.g., XLSX), and may be pluggable to support various other types of data formats. For example, the data storage 118 may be configured to receive data from one or more of the first data source 102, the second data source 104, and/or the third data source 106. Each data source 102, 104, and 106 may send data in a different file format or file type. For example, the different file formats and file types may include, but are not limited to, a CSV file, a plain-text document, an ACL document, an AMI document, an ANS document, a DBK document, a DOC document, a DOCX document, a DOT document, a DOTX document, an EPUB document, a GDOC document, an OMNI document, a PAGES document, a PDF document, a RTF document, an XHTML document, an XML document, or an XPS document. The data storage 118 may store these files in the format that they are received in. Additionally, or alternatively, while the data storage 118 has been described as storing data, the data storage 118 may also, or alternatively, be configured to request and/or access data from the data sources 102, 104, 106 with or without storing that data in the memory 116 of the system 108.

The parser component 120 may be configured to perform the parsing process described herein. For example, the parser component 120 may generate and store multiple different types of parsers that are associated with a specific file type. The file type may include any file type capable of storing data, such as healthcare related data. The parser component 120 may be configured to select a parser to parse data in a file received from one of the first data source 102, the second data source 104, and/or the third data source 106 and stored in the data storage 118. For example, a file received from the first data source 102, the second data source 104, and/or the third data source 106 may be in any number of file types. Each file type may store data in a different location of the file and/or in a different format. The parser component 120 may determine a file type of the file by, by way of example, performing a regex search on the file in order to identify a sequence of characters or a pattern that matches a predetermined category. Each parser may be associated with at least one of the predetermined categories and/or a regex category and the parser component 120 may then select the appropriate parser to be used to extract the usable data in the file based on the category in which the file is associated with and the associated parser. Selecting the appropriate parser, by the parser component 120, allows the parser to automatically extract the usable data from the file without the need for a user to do so manually. The types of information that the parser may extract may include prescription data, insurance claims data, medical claim data, pharmacy claim data, clinical data, financial data, data from The Centers for Medicare and Medicaid Services (CMS), patient data, etc.

The transformation component 122 may be configured to transform data received from the first data source 102, the second data source 104, and/or the third data source 106. A transformation of data may include a manipulation of data, such as merging data, filtering data, aggregating data, analytics of data, snapshotting data, and/or de-duplication of pieces of data. The transformation component 122 may receive a selection from a user, such as a data scientist, of an input or, multiple inputs, to be incorporated into a transformation. Inputs may be in the form of a file or a table and may include, but are not limited to, provider relationship data, billing entities data, claims data, etc. The transformation component 122 may then receive instructions from the user specifying details of the transformation. For instance, the user may provide query information that indicates a file to be used and/or parameters of the transformation. Once the input information and the query information have been received, the transformation component 122 may provide an output that includes a table and/or file that shows a result of the transformation of the inputs. In some cases the transportation component 122 may be operated locally or in some cases the transportation component 122 may be operated on another system, such as Airflow.

The monitoring component 124 may be configured to monitor data received from the first data source 102, the second data source 104, and/or the third data source 106. For example, the files received from the data sources 102, 103, and 104 may include values to be used by the parser component 120 and/or to be used in a transformation via the transformation component 122. If one of these values contains an error, the end-result of the desired analysis may be compromised. The monitoring component 124 may be configured analyze values and/or data structures within the files received from the first data source 102, the second data source 104, and/or the third data source 106. For example, the monitoring component 124 may be configured to analyze column numbers and row numbers within a file received from the first data source 102, the second data source 104, and/or the third data source 106 and determine if a row or column is missing or has been added. In some instances, the monitoring component 124 may be configured to determine if a value located within a file received from the first data source 102, the second data source 104, and/or the third data source 106 is above a predetermined threshold or below a predetermined threshold. The monitoring component 124 may compare the row number, column number, and/or the values of the files received from the first data source 102, the second data source 104, and/or the third data source 106 to previously received files containing the same or similar types of information. In some cases, an error may include determining that at least one input is not defined. For example, the monitoring component 124 may determine that at least one table used in a SQL query is not present in an input and that the transformation will not function properly with the missing table. If the monitoring component 124 determines that there is an error contained in the files, then the monitoring component 124 may send a notification to a user associated with the system 108 (e.g., a data scientist, engineer, etc.) indicating that an error is present. The notification may also indicate identifying information related to the file, such as a source identifier, file identifier, a location in the file, and/or a type of error. In some examples, the monitoring component 124 may automatically reverse a transformation to a previous state in response to detecting an error. This may prevent propagation of the error into later transformations. In some examples, the monitoring component 124 may include a platform for a user to test a particular transform. For example, the monitoring component 124 may enable the user to enter mock input and/or mock outputs (e.g., SQL mock inputs/outputs) in order to test the functionality of a transformation.

The pipelining component 126 may be configured to generate pipelines of interconnected transformations. A pipeline may include a dependency graph that includes multiple transformations and information related to those transformations. For example, the transformation component 122 may receive a selection from a user, such as a data scientist, of an input or, multiple inputs, to be incorporated into a transformation. Inputs may be in the form of a file or a table and may include, but are not limited to, provider relationship data, billing entities data, claims data, etc. Once the input information and the parameters of the transformation have been received, the transformation component 122 may provide an output that includes a table and/or file that shows a result of the transformation of the inputs. Each output of a transformation may be used as an input for a subsequent transformation. In some cases, the output may be usable for testing if the transformation functioned properly. For example, a user may wish to obtain a value that depends on information from multiple different sources and that requires the data provided from the multiple different sources to be parsed and transformed multiple times. The pipelining component 126 may generate a pipeline to organize the transformation of the multiple sets of data such that a user can easily determine where individual sets of data originated from and how they were transformed. In some examples, the pipelining component 126 may store information associated with each transformation of the pipeline such that a user may determine values of the inputs of each transformation, values of the outputs of each transformation, an author of the transformation, etc.

Referring back to FIG. 1, the system 108 may receive a file from one of the sources 102, 104, and/or 106 and may store the file in the data storage 118. The file may be in any one of multiple different file types and may include healthcare related information, such as insurance claims information, patient data, medical claim data, pharmacy claim data, clinical data, financial data, data from The Centers for Medicare and Medicaid Services (CMS), prescription data, etc. The parser component 120 may identify a file type associated with the file based at least in part on a source of the file and/or metadata associated with the file. For example, the parser component 120 may determine a file type of the file by, by way of example, performing a regex search on the file in order to identify a sequence of characters or a pattern that matches a predetermined category. Each parser may be associated with at least one of the predetermined categories and/or a regex category and the parser component 120 may then select the appropriate parser to be used to extract the usable data in the file based on the category in which the file is associated with and the associated parser. Selecting the appropriate parser, by the parser component 120, allows the parser to automatically extract the usable data from the file without the need for a user to do so manually. In some cases, the parser component 120 may determine that a certain type of data matches a type of data that was previously extracted. For example, the parser component 120 may determine that the data includes updated insurance claims data from a particular source and that the updated insurance claims data matches previously received insurance claims data from the same source. In this case, the parser component 120 may update a value that represents the insurance claims data associated with the source to reflect the updated insurance claims data. In some cases, the parsed data may be stored as tables and stored in the data storage 118. Once the data from the file has been parsed, the system 108 may receive instructions from a user 128 via a computing device 130 to perform a transformation on the data. The transformation component 122 may store multiple different types of transformations that can be performed on the data, such as merging data, filtering data, and/or de-duplication of pieces of data. The transformation component 122 may receive a selection from the user 128 via the computing device 130 of inputs to be incorporated in the transformation. The inputs may include a table representative of the different data sets extracted from the file by the parser component 120. The transformation component 122 may provide an output in the form of a table that includes the result of the transformation of the input. The pipeline component 126 may generate a dependency graph that links multiple transformations. For example, the input of a transformation may depend on the output of a previous transformation, forming a pipeline of dependent transformations that originates from the file received by the sources 102, 104, and/or 106. Once a pipeline has been established, the monitoring component 124 may compare the row number, column number, and/or the values of subsequently received files to previously received files containing the same or similar types of information. If the monitoring component 124 determines that there is an error contained in the files, then the monitoring component 124 may send a notification to a user associated with the system 108 (e.g., a data scientist, engineer, etc.) indicating that an error is present.

As used herein, a processor, such as processor(s) 112, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 112 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 112 may possess its own local memory, which also may store program components, program data, and/or one or more operating systems.

The memory 116 may include volatile and nonvolatile memory, removable and non-removable media implemented in any method or technology for storage of information, such as computer-readable instructions, data structures, program component, or other data. Such memory 116 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 116 may be implemented as computer-readable storage media ("CRSM"), which may be any available physical media accessible by the processor(s) 112 to execute instructions stored on the memory 116. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, each respective memory, such as memory 116, discussed herein may include at least one operating system (OS) component that is configured to manage hardware resource devices such as the network interface(s), the I/O devices of the respective apparatuses, and so forth, and provide various services to applications or components executing on the processors. Such OS component may implement a variant of the FreeBSD operating system as promulgated by the FreeBSD Project; other UNIX or UNIX-like variants; a variation of the Linux operating system as promulgated by Linus Torvalds; the FireOS operating system from Amazon.com Inc. of Seattle, Wash., USA; the Windows operating system from Microsoft Corporation of Redmond, Wash., USA; LynxOS as promulgated by Lynx Software Technologies, Inc. of San Jose, Calif.; Operating System Embedded (Enea OSE) as promulgated by ENEA AB of Sweden; and so forth.

The network interface(s) 114 may enable communications between the components and/or devices shown in environment 100 and/or with one or more other remote systems, as well as other networked devices. Such network interface(s) 114 may include one or more network interface controllers (NICs) or other types of transceiver devices to send and receive communications over the network 110.

For instance, each of the network interface(s) 114 may include a personal area network (PAN) component to enable communications over one or more short-range wireless communication channels. For instance, the PAN component may enable communications compliant with at least one of the following standards IEEE 802.15.4 (ZigBee), IEEE 802.15.1 (Bluetooth), IEEE 802.11 (WiFi), or any other PAN communication protocol. Furthermore, each of the network interface(s) 114 may include a wide area network (WAN) component to enable communication over a wide area network.

Figure 2:
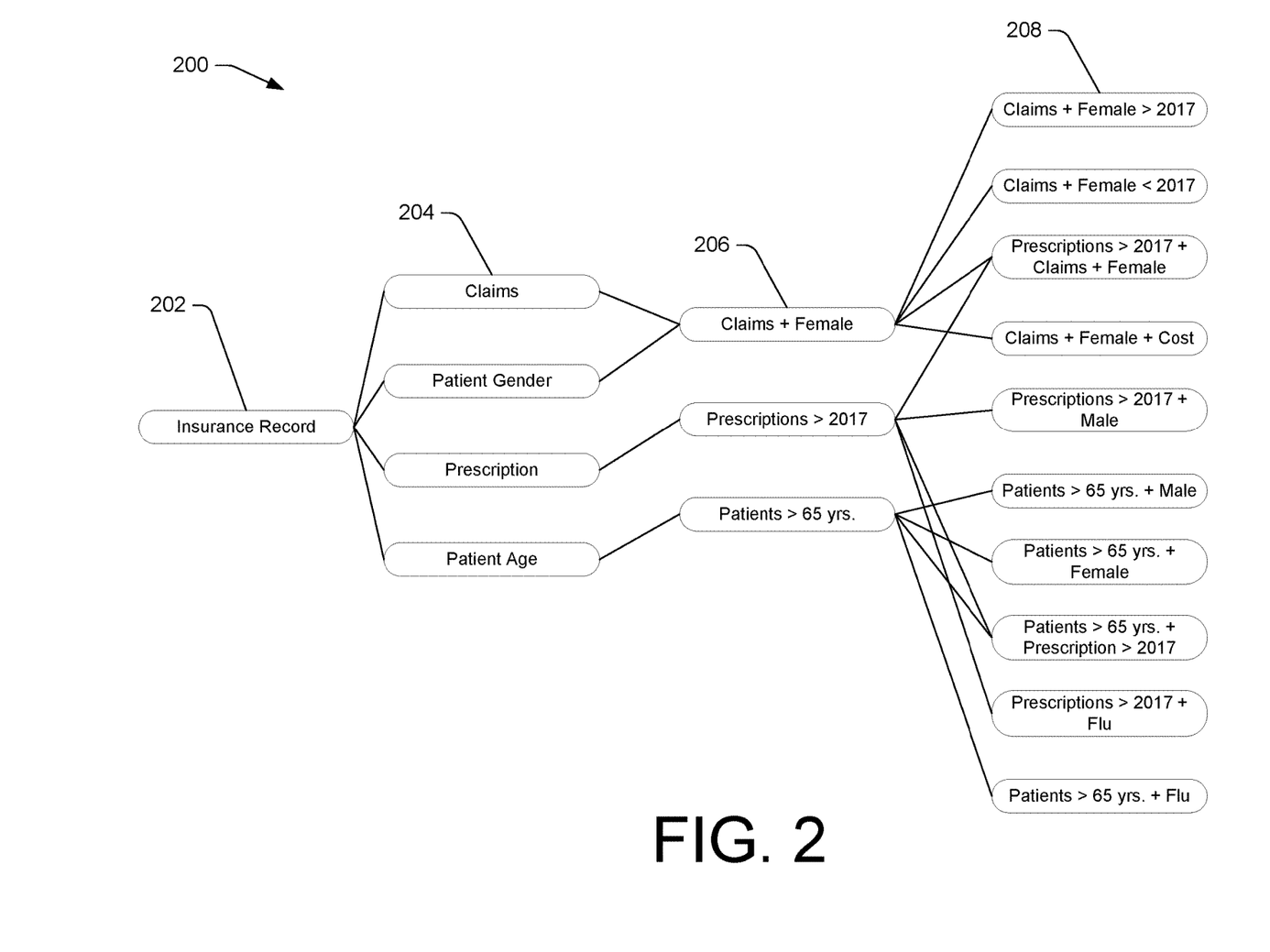
FIG. 2 illustrates a diagram of an example pipeline of data.

FIG. 2 illustrates an example pipeline 200 that may be generated by the system 108. The pipeline 200 may include a dependency graph that includes multiple transformations of data received from a data source, such as the first data source 102, the second data source 104, and/or the third data source 106. For example, the transformation component 122 may receive a selection from a user, such as the user 128 via the computing device 130, of an input or, multiple inputs, to be incorporated into a transformation. Inputs may be in the form of a file or a table and may include, but are not limited to, provider relationship data, billing entities data, claims data, etc. Once the input information and the parameters of the transformation have been received, the transformation component 122 may provide an output that includes a table and/or file that shows a result of the transformation of the inputs. The pipelining component 126 may generate a pipeline to organize the transformation of the multiple sets of data such that a user can easily determine where individual sets of data originated from and how they were transformed. In some cases, generating the pipeline may include auto-generation of the pipeline by the pipelining component 126 based on the inputs and outputs of a transformation. FIG. 2 illustrates an example pipeline 200 of an insurance record 202 and various example transformations that may be applied to the information in the insurance record 202. A first set of transformations 204 may include a filter type of transformation of the insurance record 202. The transformations 204 may include the insurance record 202 as an input and the four subsequent pipelines, claims, patient gender, prescription, and patient age, as outputs of the four different transformations. A second set of transformations 206 may include a merging transformation in which the claims output and the patient gender output from the first set of transformations 202 are used as inputs resulting in an output which includes data detailing claims for female patients. The second set of transformations 206 may also include a filter transformation in which the prescription output from the first set of transformations 204 is used as an input and filtered to provide prescriptions filled after the year 2017 and a filter transformation in which the patient age output from the first set of transformations 204 is used as an input and filtered to provide a list of patients over the age of 65 years. A third set of transformations 208 may provide various types of information based at least in part on the inputs used from the outputs of the second set of transformations 206 and the type of transformations performed on the inputs. The first set of transformations 204, the second set of transformations 206, and the third set of transformations 208 form the pipeline 200 enables a user, such as the user 128, to manipulate data received from sources, such as the first data source 102, the second data source 104, and/or the third data source 106, and to have access to a lineage depicting the source and transformation history of each piece of data. For example, each piece of data in the third set of transformations 208 may include metadata indicating all of the previous transformations performed on the data and/or an author of the transformations. A user may access any transformation in the pipeline and determine a source of the inputs and a transformation that was performed on the inputs. Although FIG. 2 illustrates an example pipeline generated for various transformations of the insurance record 202, it should be understood that a pipeline may be generated for any file received from a file source and that any number of combinations of transformations may be performed on the file, thereby generating a pipeline.

Figure 3:
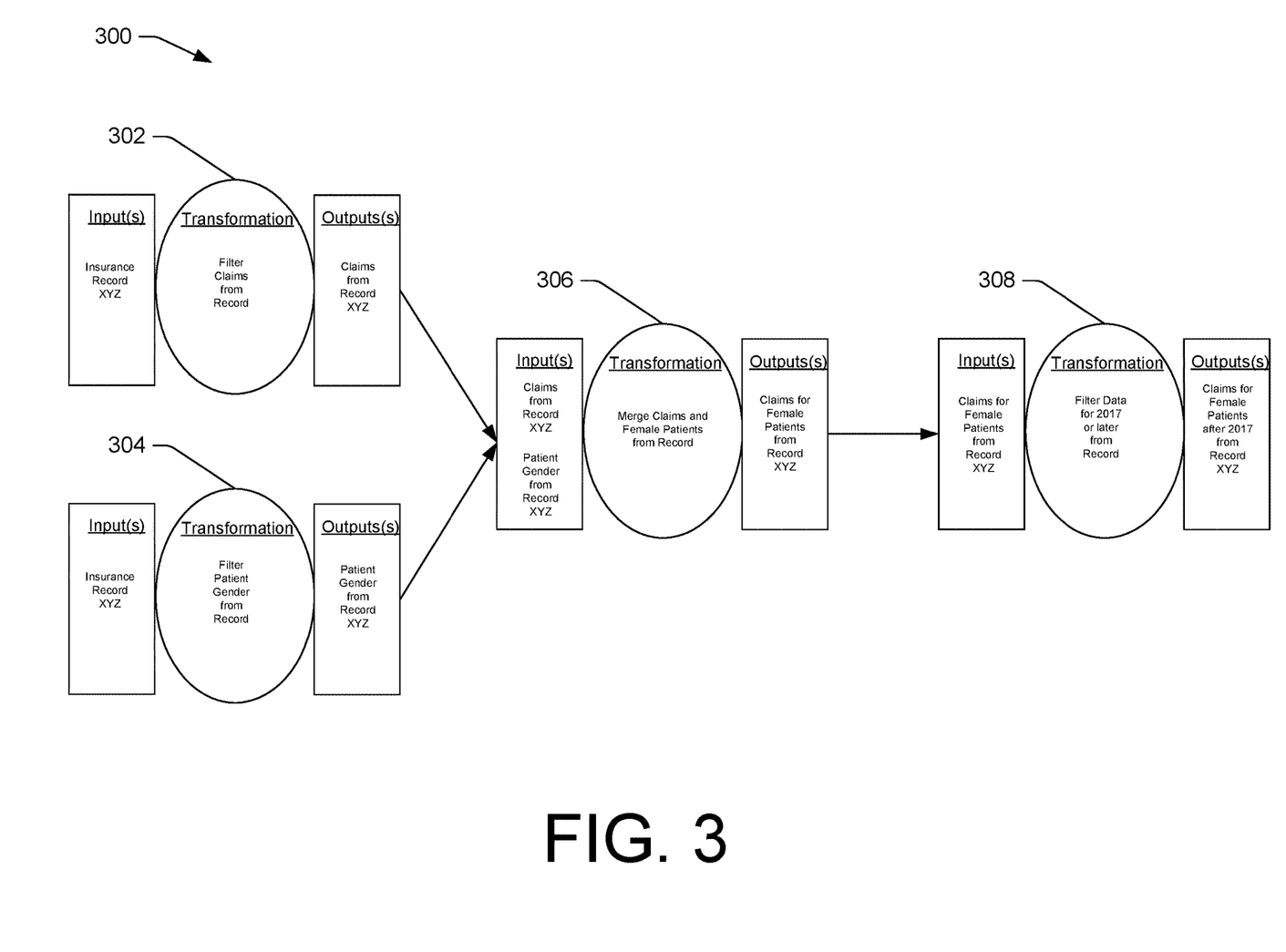
FIG. 3 illustrates a conceptual diagram of an example pipeline of data.

FIG. 3 illustrates an example pipeline pathway 300 and various transformations associated with the pathway 300. The system 108 may receive instructions from a user, such as the user 128 via the computing device 130, to perform various transformations on data contained in a file received from a source, such as the first data source 102, the second data source 104, and/or the third data source 106. In one example, the transformation component 122 may receive a selection of an input to be incorporated into a transformation. Inputs may be in the form of a file or a table and may include, but are not limited to, provider relationship data, billing entities data, claims data, etc. The transformation component 122 may then receive instructions from the user specifying details of the transformation. For instance, the user may provide query information that indicates a file to be used and/or parameters of the transformation. Once the input information and the query information have been received, the transformation component 122 may provide an output that includes a table and/or file that shows a result of the transformation of the inputs. In the illustrated example pathway 300, a first transformation 302 may include an "Insurance Record XYZ" as an input and a filter transformation in which the output includes a table of claims from the "Insurance Record XYZ." A second transformation 304 may include an "Insurance Record XYZ" as an input and a filter transformation in which the output includes a table of patient genders from the "Insurance Record XYZ." A third transformation 306 may include the outputs from the first transformation 302 and the second transformation 304 as inputs and a merge transformation in which the output includes a table of claims for female patients from the "Insurance Record XYZ." A fourth transformation 308 may include the output from the third transformation 306 as an input and a filter transformation in which the output includes a table of claims for female patients after 2017 "Insurance Record XYZ." By generating the pathway pipeline 300, the system 108 may provide a lineage depicting the source and transformation history of each piece of data contained at each of the transformations. For example, each piece of data in the transformations 302, 304, 306, and 308 may include metadata indicating all of the previous transformations performed on the data and/or an author of the transformations. A user may access any transformation in the pipeline and determine a source of the inputs and a transformation that was performed on the inputs. Although FIG. 3 illustrates an example pipeline generated for various transformations of an "Insurance Record XYZ," it should be understood that a pipeline pathway may be generated for any file received from a file source and that any number of combinations of transformations may be performed on the file, thereby generating a pipeline.

Figure 4:
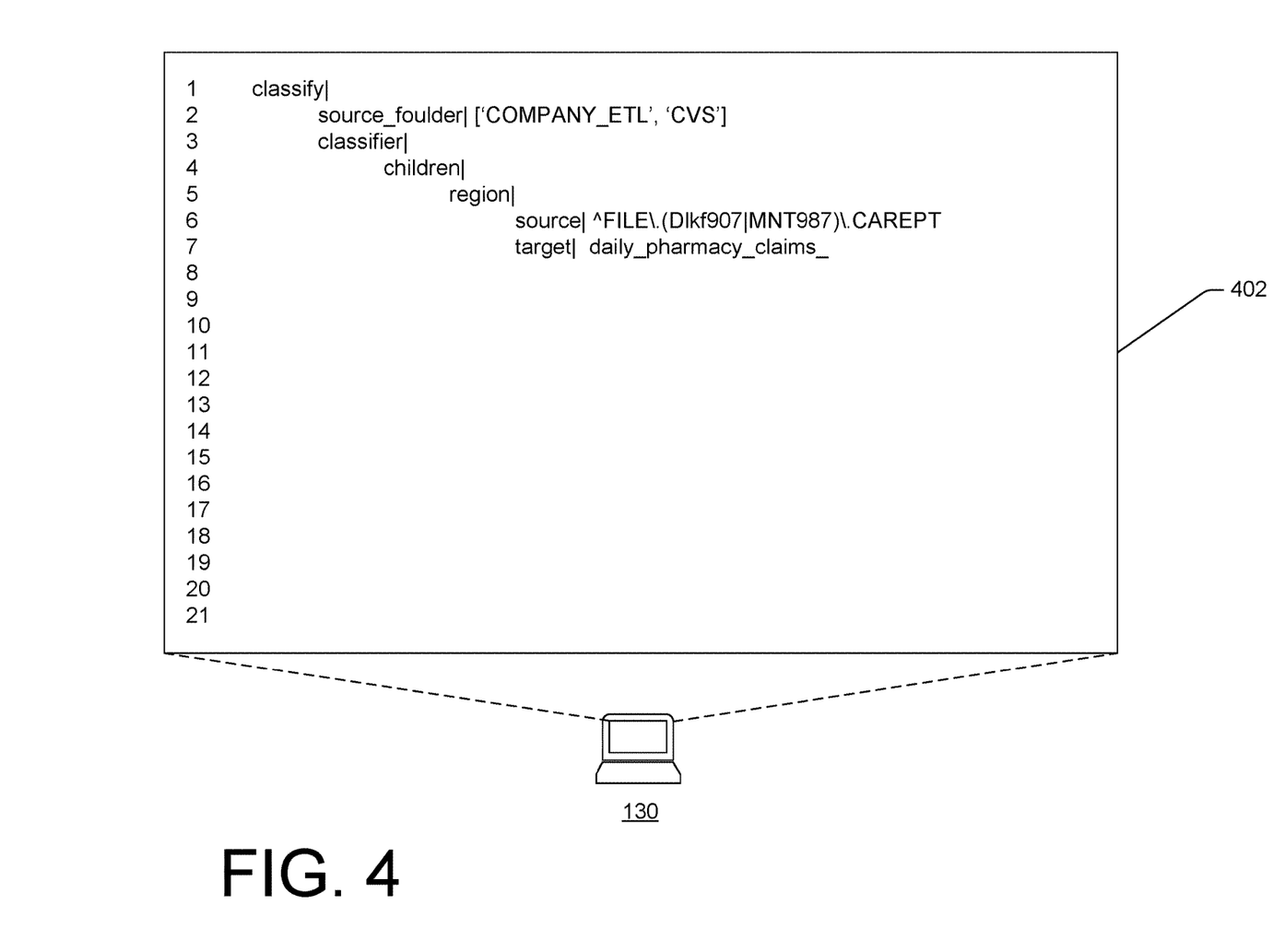
FIG. 4 illustrates an example user interface for parsing data.

FIG. 4 illustrates an example interface 402 that may be presented to a user via the computing device 130 to provide functionality to allow the user to access and parse a file received from a source, such as the data sources 102, 103, and/or 104. The interface 402 may include multiple lines with each line providing a different level of information or an instruction. For example, line 1 of the interface 402 may include a "classify" instruction which may cause the system 108 to determine a file type of a file received from the data sources 102, 103, and/or 104. Line 2 of the interface 402 may include source folder information and, as shown in the example interface 402, the source folder may be a "['COMPANY_ETL', 'CVS']" file. Line 3 of the interface may include a classifier instruction that may delineate the file based at least in part on the content in the file, such has by children and by region as shown in lines 4 and 5. Lines 6 and 7 of the interface 402 may depict a target value, such as "daily_pharmacy_claims" and a source of the target, such as "^FILE\.(Dlkf907|MNT987)\.CAREPT." The files accessed and parsed via the interface 402 may be stored in the data storage 118 and may be accessed by the parser component 120.

Figure 5:
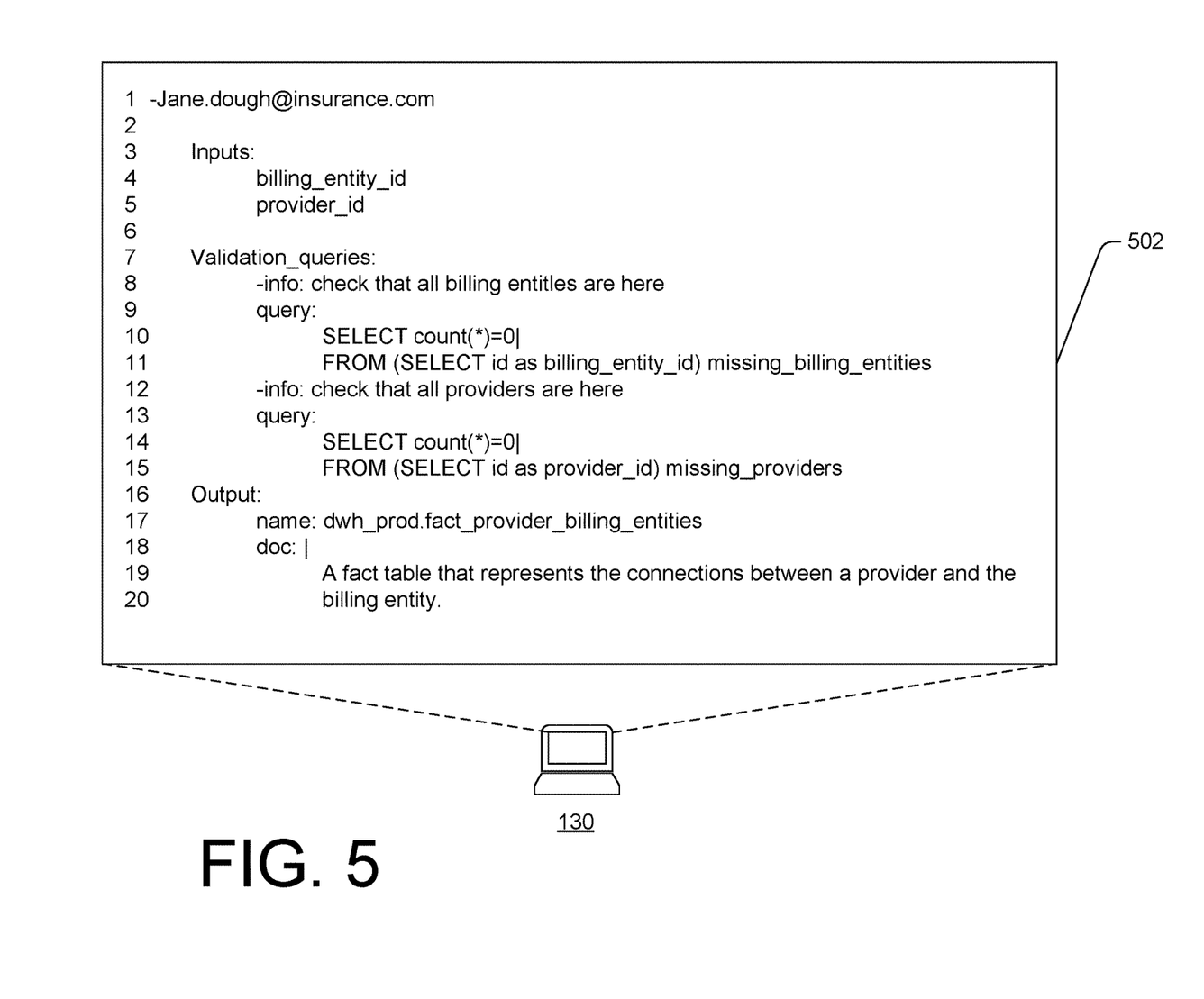
FIG. 5 illustrates an example user interface for transforming data.

FIG. 5 illustrates an example interface 502 that may be presented to a user via the computing device 130 to provide functionality to allow a user to access and transform data from a file received from a source, such as the data sources 102, 103, and/or 104. The interface 502 may include an identification of a user at line 1. The interface 502 may request a credential, such as a username or a password, of the user when accessing the interface 502 to determine an identity of the user. The interface 502 may include multiple inputs, such as "billing_entity_id" and "provider_id." The inputs may include links to files and/or tables containing data stored in the data storage 118. The user interface 502 may include instructions from the user specifying details of the transformation. For instance, the user may provide query information that indicates a file to be used and/or parameters of the transformation. In the example shown in FIG. 5, the query may be a validation query searching for missing billing entities and missing providers. Once the input information and the query information have been received, the transformation component 122, via the interface 502 may provide an output that includes a table and/or file that shows a result of the transformation of the inputs. In the example shown in FIG. 5, the output may include a link to a file or table that represents connections between a provider and a billing entity.

Figure 6:
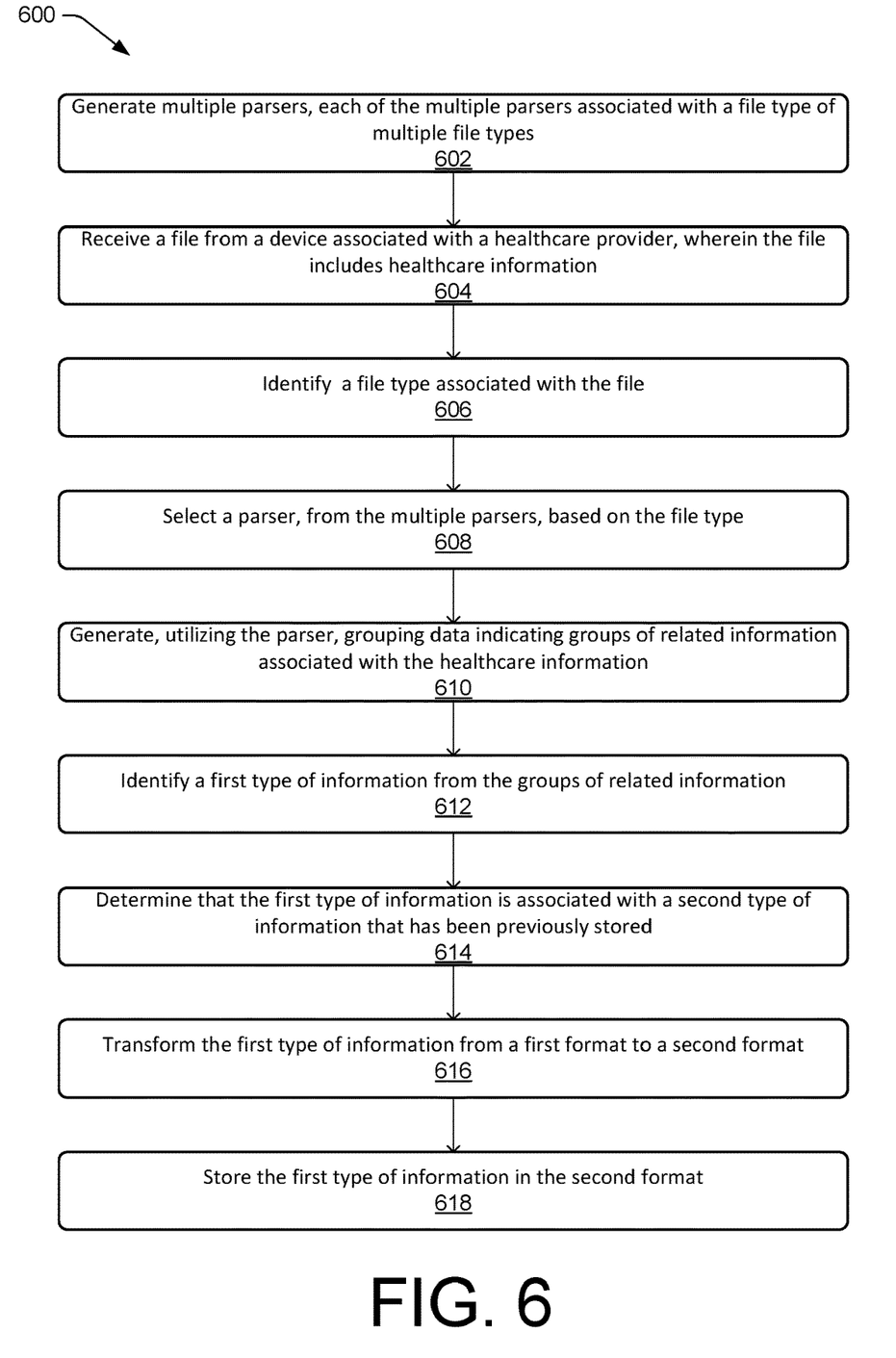
FIG. 6 illustrates a flow diagram of an example process for transforming data.
Figure 7:
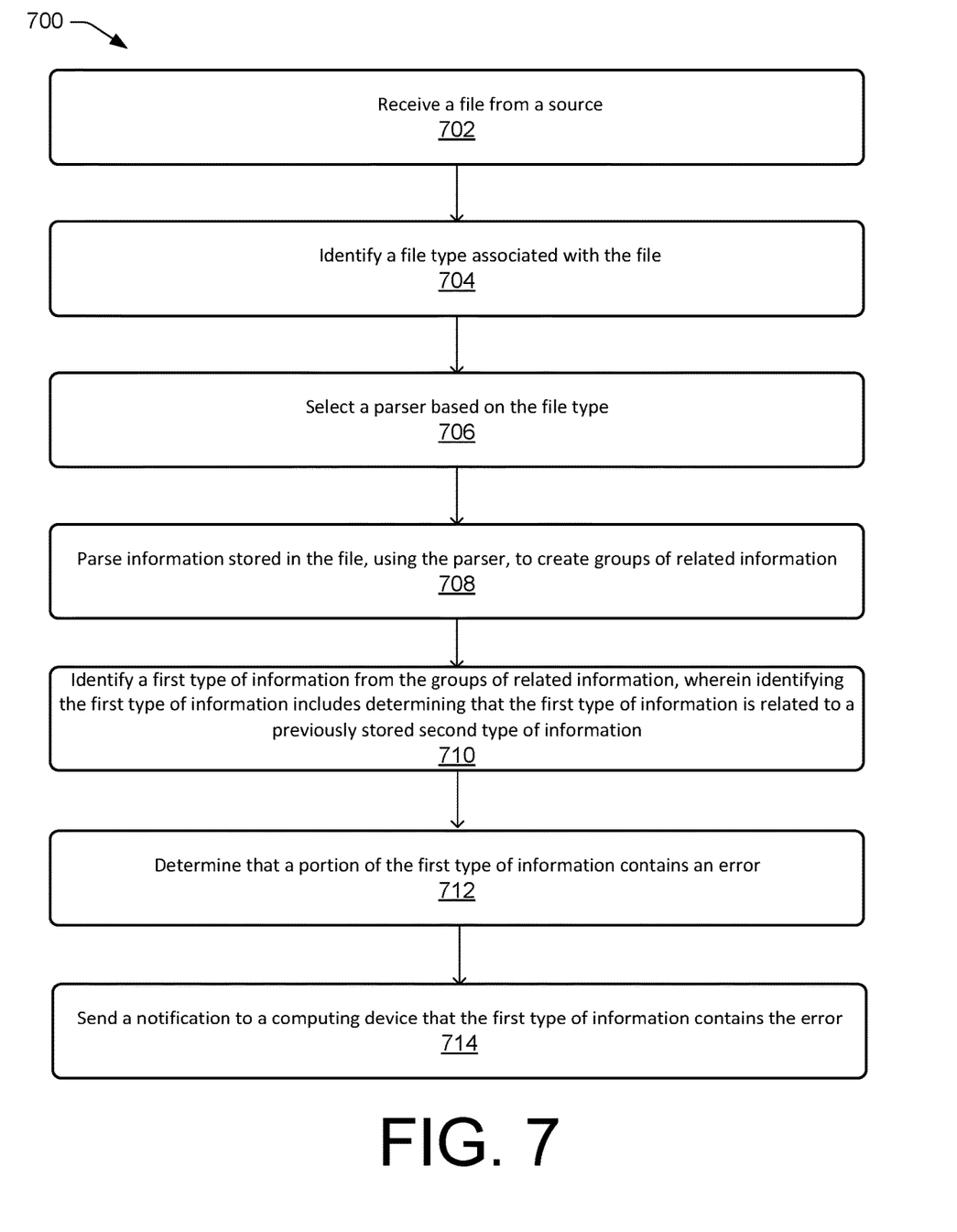
FIG. 7 illustrates a flow diagram of an example process for monitoring data.

FIGS. 6 and 7 illustrate various processes for transforming and pipelining data. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-5, although the processes may be implemented in a wide variety of other environments, architectures and systems.

FIG. 6 illustrates a flow diagram of an example process 600 for receiving files and transforming information in the files. The order in which the operations or steps are described is not intended to be construed as a limitation, and any number of the described operations may be combined in any order and/o in parallel to implement process 600.

At block 602, the process 600 may include generating multiple parsers, each of the multiple parsers associated with a file type of multiple file types. For example, the parser component 120 may generate and store multiple different types of parsers that are associated with a specific file type. The file type may include any file type capable of storing data, such as healthcare related data. The parser component 120 may be configured to select a parser to parse data in a file received from one of the first data source 102, the second data source 104, and/or the third data source 106 and stored in the data storage 118.

At block 604, the process 600 may include receiving a file from a device associated with a healthcare provider, wherein the file includes healthcare information. For example, as shown in FIG. 1, each of the first data source 102, the second data source 104, and the third data source 106 represent a remote system that generates and/or acquires data associated with one or more people and stores that data, such as in a database associated with the first data source 102, the second data source 104, or the third data source 106. By way of example, the first data source 102 may be a hospital, clinic, and/or other type of healthcare provider. The second data source 104 may be a pharmacy that receives and fulfills prescriptions. The third data source 106 may be an insurance company that processes claims from the first data source 102, the second data source 104, or any other healthcare related entity. The first data source 102, the second data source 104, and/or the third data source 106 may communicate with a system 108 via one or more networks 110. The communication may include the sending and/or receiving of data associated with a person and/or people associated with a given data source. The data storage 118 may be configured to store data received by the system 108. For example, the data storage 118 may be configured to receive data from one or more of the first data source 102, the second data source 104, and/or the third data source 106.

At block 606, the process 600 may include identifying a file type associated with the file. For example, the system 108 may identify a file type based at least in part on metadata associated with the file and/or a source of the file. In some examples, parser component 120 may determine a file type of the file by, by way of example, performing a regex search on the file in order to identify a sequence of characters or a pattern that matches a predetermined category. Each parser may be associated with at least one of the predetermined categories and/or a regex category and the parser component 120 may then select the appropriate parser to be used to extract the usable data in the file based on the category in which the file is associated with and the associated parser. Each data source 102, 104, and 106 may send data in a different file format or file type. For example, the different file formats and file types may include, but are not limited to, a CSV file, a plain-text document, an ACL document, an AMI document, an ANS document, a DBK document, a DOC document, a DOCX document, a DOT document, a DOTX document, an EPUB document, a GDOC document, an OMNI document, a PAGES document, a PDF document, a RTF document, an XHTML document, an XML document, or an XPS document. The data storage 118 may store these files in the format that they are received in. Additionally, or alternatively, while the data storage 118 has been described as storing data, the data storage 118 may also, or alternatively, be configured to request and/or access data from the data sources 102, 104, 106 with or without storing that data in the memory 116 of the system 108.

At block 608, the process 600 may include selecting a parser, from the multiple parsers, based at least in part on the file type. For example, a file received from the first data source 102, the second data source 104, and/or the third data source 106 may be in any number of file types. Each file type may store data in a different location of the file and/or in a different format. The parser component 120 may determine a file type of the file by, by way of example, performing a regex search on the file in order to identify a sequence of characters or a pattern that matches a predetermined category. Each parser may be associated with at least one of the predetermined categories and/or a regex category and the parser component 120 may then select the appropriate parser to be used to extract the usable data in the file based on the category in which the file is associated with and the associated parser.

At block 610, the process 600 may include generating, utilizing the parser, grouping data indicating groups of related information associated with the healthcare information. For example, the parser component 120 may generate and store multiple different types of parsers that are associated with a specific file type. The file type may include any file type capable of storing data, such as healthcare related data. The parser component 120 may be configured to select a parser to parse data in a file received from one of the first data source 102, the second data source 104, and/or the third data source 106 and stored in the data storage 118. For example, a file received from the first data source 102, the second data source 104, and/or the third data source 106 may be in any number of file types. Each file type may store data in a different location of the file and/or in a different format. The parser component 120 may determine a file type of the file by, by way of example, performing a regex search on the file in order to identify a sequence of characters or a pattern that matches a predetermined category. Each parser may be associated with at least one of the predetermined categories and/or a regex category and the parser component 120 may then select the appropriate parser to be used to extract the usable data in the file based on the category in which the file is associated with and the associated parser. Selecting the appropriate parser, by the parser component 120, allows the parser to automatically extract the usable data from the file without the need for a user to do so manually. The types of information that the parser may extract may include prescription data, insurance claims data, patient data, etc.

At block 612, the process 600 may include identifying a first type of information from the groups of related information and at block 614, the process 600 may include determining that the first type of information is associated with a second type of information that has been previously stored. For example, electing the appropriate parser, by the parser component 120, allows the parser to automatically extract the usable data from the file without the need for a user to do so manually. In some cases, the parser component 120 may determine that a certain type of data matches a type of data that was previously extracted. For example, the parser component 120 may determine that the data includes updated insurance claims data from a particular source and that the updated insurance claims data matches previously received insurance claims data from the same source. In this case, the parser component 120 may update a value that represents the insurance claims data associated with the source to reflect the updated insurance claims data.

At block 616, the process 600 may include transforming the first type of information from a first format to a second format. For example, the transformation component 122 may be configured to transform data received from the first data source 102, the second data source 104, and/or the third data source 106. A transformation of data may include a manipulation of data, such as merging data, filtering data, and/or de-duplication of pieces of data. The transformation component 122 may receive a selection from a user, such as a data scientist, of an input or, multiple inputs, to be incorporated into a transformation. Inputs may be in the form of a file or a table and may include, but are not limited to, provider relationship data, billing entities data, claims data, etc. The transformation component 122 may then receive instructions from the user specifying details of the transformation. For instance, the user may provide query information that indicates a file to be used and/or parameters of the transformation. Once the input information and the query information have been received, the transformation component 122 may provide an output that includes a table and/or file that shows a result of the transformation of the inputs.

At block 618, the process 600 may include storing the first type of information in the second format. For example, the data storage 118 may be configured to store data received by the system 108 and/or transformed by the system 108.

FIG. 7 illustrates a flow diagram of an example process 700 for receiving files from a source and monitoring the values in the file. The order in which the operations or steps are described is not intended to be construed as a limitation, and any number of the described operations may be combined in any order and/or in parallel to implement process 700.

At block 702, the process 700 may include receiving a file from a source. For example, as shown in FIG. 1, each of the first data source 102, the second data source 104, and the third data source 106 represent a remote system that generates and/or acquires data associated with one or more people and stores that data, such as in a database associated with the first data source 102, the second data source 104, or the third data source 106. By way of example, the first data source 102 may be a hospital, clinic, and/or other type of healthcare provider. The second data source 104 may be a pharmacy that receives and fulfills prescriptions. The third data source 106 may be an insurance company that processes claims from the first data source 102, the second data source 104, or any other healthcare related entity. The first data source 102, the second data source 104, and/or the third data source 106 may communicate with a system 108 via one or more networks 110. The communication may include the sending and/or receiving of data associated with a person and/or people associated with a given data source. The data storage 118 may be configured to store data received by the system 108. For example, the data storage 118 may be configured to receive data from one or more of the first data source 102, the second data source 104, and/or the third data source 106.

At block 704, the process 700 may include identifying a file type associated with the file. For example, the system 108 may identify a file type based at least in part on metadata associated with the file and/or a source of the file. In some instances, parser component 120 may determine a file type of the file by, by way of example, performing a regex search on the file in order to identify a sequence of characters or a pattern that matches a predetermined category. Each parser may be associated with at least one of the predetermined categories and/or a regex category and the parser component 120 may then select the appropriate parser to be used to extract the usable data in the file based on the category in which the file is associated with and the associated parser. Each data source 102, 104, and 106 may send data in a different file format or file type. For example, the different file formats and file types may include, but are not limited to, a CSV file, a plain-text document, an ACL document, an AMI document, an ANS document, a DBK document, a DOC document, a DOCX document, a DOT document, a DOTX document, an EPUB document, a GDOC document, an OMNI document, a PAGES document, a PDF document, a RTF document, an XHTML document, an XML document, or an XPS document. The data storage 118 may store these files in the format that they are received in. Additionally, or alternatively, while the data storage 118 has been described as storing data, the data storage 118 may also, or alternatively, be configured to request and/or access data from the data sources 102, 104, 106 with or without storing that data in the memory 116 of the system 108.

At block 706, the process 700 may include selecting a parser based at least in part on the file type. For example, a file received from the first data source 102, the second data source 104, and/or the third data source 106 may be in any number of file types. Each file type may store data in a different location of the file and/or in a different format. The parser component 120 may determine a file type of the file by, by way of example, performing a regex search on the file in order to identify a sequence of characters or a pattern that matches a predetermined category. Each parser may be associated with at least one of the predetermined categories and/or a regex category and the parser component 120 may then select the appropriate parser to be used to extract the usable data in the file based on the category in which the file is associated with and the associated parser.

At block 708, the process 700 may include parsing information stored in the file, using the parser, to create groups of related information. For example, the parser component 120 may generate and store multiple different types of parsers that are associated with a specific file type. The file type may include any file type capable of storing data, such as healthcare related data. The parser component 120 may be configured to select a parser to parse data in a file received from one of the first data source 102, the second data source 104, and/or the third data source 106 and stored in the data storage 118. For example, a file received from the first data source 102, the second data source 104, and/or the third data source 106 may be in any number of file types. Each file type may store data in a different location of the file and/or in a different format. The parser component 120 may determine a file type of the file by, by way of example, performing a regex search on the file in order to identify a sequence of characters or a pattern that matches a predetermined category. Each parser may be associated with at least one of the predetermined categories and/or a regex category and the parser component 120 may then select the appropriate parser to be used to extract the usable data in the file based on the category in which the file is associated with and the associated parser. Selecting the appropriate parser, by the parser component 120, allows the parser to automatically extract the usable data from the file without the need for a user to do so manually. The types of information that the parser may extract may include prescription data, insurance claims data, patient data, etc.

At block 710, the process 700 may include identifying a first type of information from the groups of related information, wherein identifying the first type of information includes determining that the first type of information is related to a previously stored second type of information. For example, electing the appropriate parser, by the parser component 120, allows the parser to automatically extract the usable data from the file without the need for a user to do so manually. In some cases, the parser component 120 may determine that a certain type of data matches a type of data that was previously extracted. For example, the parser component 120 may determine that the data includes updated insurance claims data from a particular source and that the updated insurance claims data matches previously received insurance claims data from the same source. In this case, the parser component 120 may update a value that represents the insurance claims data associated with the source to reflect the updated insurance claims data.

At block 712, the process 700 may include determining that a portion of the first type of information contains an error. For example, the monitoring component 124 may be configured to monitor data received from the first data source 102, the second data source 104, and/or the third data source 106. For example, the files received from the data sources 102, 103, and 104 may include values to be used by the parser component 120 and/or to be used in a transformation via the transformation component 122. If one of these values contains an error, the end-result of the desired analysis may be compromised. The monitoring component 124 may be configured analyze values and/or data structures within the files received from the first data source 102, the second data source 104, and/or the third data source 106. For example, the monitoring component 124 may be configured to analyze column numbers and row numbers within a file received from the first data source 102, the second data source 104, and/or the third data source 106 and determine if a row or column is missing or has been added. In some instances, the monitoring component 124 may be configured to determine if a value located within a file received from the first data source 102, the second data source 104, and/or the third data source 106 is above a predetermined threshold or below a predetermined threshold. The monitoring component 124 may compare the row number, column number, and/or the values of the files received from the first data source 102, the second data source 104, and/or the third data source 106 to previously received files containing the same or similar types of information.

At block 714, the process 700 may include sending a notification to a computing device that the first type of information contains the error. For example, if the monitoring component 124 determines that there is an error contained in the files, then the monitoring component 124 may send a notification to a user associated with the system 108 (e.g., a data scientist, engineer, etc.) indicating that an error is present. The notification may also indicate identifying information related to the file, such as a source identifier, file identifier, a location in the file, and/or a type of error.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A system comprising:
one or more processors; and
computer-readable media storing computer-executable instructions that, when executed by the one or more processors, cause the one or more processors to perform operations comprising:
generating multiple parsers, each of the multiple parsers associated with a file type of multiple file types;
receiving a file from a device associated with a healthcare provider, wherein the file includes healthcare information;
identifying a file type associated with the file, wherein the file type corresponds to at least one of a binary file-type, a CSV file, a plain-text document, an ACL document, an AMI document, an ANS document, a DBK document, a DOC document, a DOCX document, a DOT document, a DOTX document, an EPUB document, a GDOC document, an OMM document, a PAGES document, a PDF document, a RTF document, an XHTML document, an XML document, or an XPS document;
selecting a parser, from the multiple parsers, based at least in part on the file type;
generating, utilizing the parser, grouping data indicating groups of related information associated with the healthcare information;

identifying a first type of information from the groups of related information;
determining that the first type of information is associated with a second type of information that has been previously stored;
transforming the first type of information from a first format to a second format, wherein the second format includes at least one of merging the first type of information with a third type of information, filtering the first type of information, or de-duplicating the first type of information; and
storing the first type of information in the second format.

2. The system of claim 1, the operations further comprising:
determining that the first type of information includes data associated with a first database; and
wherein storing the first type of information comprises storing the first type of information in association with the database.

3. The system of claim 1, the operations further comprising:
transforming the first type of information from the second format to a third format; and
generating a table associated with the first type of information, the table indicating a record of transformations including transforming the first type of information from the second format to the third format.

4. The system of claim 3, wherein the record indicates at least one of the file type, an author identifier of the file, a source identifier of the file, a date identifier for when the file was updated, a time identifier for when the file was updated, or a list of previous transformations associated with the first type of information.

5. The method of claim 4, further comprising:
receiving a request to access the healthcare information corresponding to the first type of information; and
based at least in part on receiving the request, causing display of a representation of the healthcare information and the table.

6. The system of claim 5, wherein the representation of the healthcare information and the table include at least one of:
an identification of a data pipeline that the first type of information was transmitted on;
an author of the first type of information;
an identification of an entity associated with transforming the first type of information; or
an identification of a type of the parser.

7. A method comprising:
receiving a file from a source;
identifying at least one of a file type or a file version associated with the file;
selecting a parser based at least in part on the at least one of the file type or the file version;
generating, utilizing the parser, grouping data indicating groups of related information associated with the file;
identifying a first type of information from the groups of related information;
determining that the first type of information is associated with a second type of information that has been previously stored;
transforming the first type of information from a first format to a second format; and
storing the first type of information in the second format.

8. The method of claim 7, further comprising:
determining that the first type of information includes data associated with a first database; and
wherein storing the first type of information comprises storing the first type of information in association with the database.

9. The method of claim 8, wherein the source comprises a first source and the database is associated with at least one of:
at least one of the first source or a second source;
an internal database; or
the parser.

10. The method of claim 9, wherein the database is a first database and is associated with the internal database, the internal database including at least a second database that stores a third type of information.

11. The method of claim 10, wherein the file includes a first file and at least one of:
the first type of information and the second type of information originated from the first file; or
the first type of information originated from the first file and the second type of information originated from a second file that is different than the first file.

12. The method of claim 7, wherein identifying the at least one of the file type or the file version includes scanning the file and identifying information that indicates at least one of the file type or file version.

13. The method of claim 7, wherein generating the grouping data includes:
determining a location in the file that includes relevant content based at least in part on at least one of the file type or the file version;
extracting the relevant content from the file; and
storing the relevant content in association with the parser to create the groups of related data.

14. The method of claim 7, wherein transforming the first type of information from the first format to the second format includes at least one of:
merging the first type of information with a third type of information;
filtering the first type of information; or
de-duplicating the first type of information.

15. A system comprising:
one or more processors; and
computer-readable media storing computer-executable instructions that, when executed by the one or more processors, cause the one or more processors to perform operations comprising:
receiving a file from a source;
identifying a file type associated with the file;
selecting a parser based at least in part on the file type;
generating, utilizing the parser, grouping data indicating groups of related information associated with the file;
identifying a first type of information from the groups of related information;
determining that the first type of information is associated with a second type of information that has been previously stored;
determining that a portion of information corresponding to the first type of information contains an error; and
sending a notification to a computing device that the portion of information corresponding to the first type of information contains the error.

16. The system of claim 15, wherein the notification includes at least one of:

an indication that an incorrect number of rows and/or columns is located in the file;

an indication that a value located in the file has not been updated over a threshold number of days;

an indication that a value located in the file is above or below an average value by a threshold amount;

an indication that a value located in the file is above or below a median value by a threshold amount;

an indication that a value located in the file is above or below a minimum value by a threshold amount;

an indication that a value located in the file is above or below a maximum value by a threshold amount; or an indication that a value located in the file is zero.

17. The system of claim 15, further comprising receiving monitoring settings wherein determining that the portion of information corresponding to the first type of information contains an error is based at least in part on the monitoring settings.

18. The system of claim 17, wherein the monitoring settings include at least one of:

determining that the portion of information corresponding to the first type of information contains an error in response to a value located in the file being zero; or determining that the portion of information corresponding to the first type of information contains an error in response to a value located in the file being above or below a percentage.

19. The system of claim 15, wherein the second computing device includes a data monitoring service vendor.

20. The system of claim 15, wherein the notification includes a first notification, the operations further comprising sending a second notification to the source that that the portion of information corresponding to the first type of information contains the error.

* * * * *